United States Patent [19]
Jain et al.

[11] Patent Number: 5,962,667
[45] Date of Patent: Oct. 5, 1999

[54] PHARMACO-GENE DELIVERY IN HUMAN BREAST CANCER CELLS

[75] Inventors: Pramod Jain, Glen Allen; David Gewirtz, Richmond, both of Va.

[73] Assignee: Virginia Commonwealth University, Richmond, Va.

[21] Appl. No.: 08/962,613

[22] Filed: Nov. 3, 1997

[51] Int. Cl.$^6$ .......................... C12N 15/12; C12N 15/33; C07J 1/00
[52] U.S. Cl. ...................... 536/23.1; 536/23.2; 536/23.5; 536/23.72; 540/2
[58] Field of Search ............................. 514/44, 170, 874; 424/450; 536/23.1, 23.2, 23.5, 23.72, 24.1; 540/2

[56] References Cited

U.S. PATENT DOCUMENTS

| | | | |
|---|---|---|---|
| 4,937,238 | 6/1990 | Lemon | 514/178 |
| 5,446,143 | 8/1995 | Simpson et al. | 536/24.1 |
| 5,472,985 | 12/1995 | Grainger et al. | 514/651 |
| 5,527,884 | 6/1996 | Russell et al. | 530/350 |
| 5,545,569 | 8/1996 | Grainger et al. | 436/518 |
| 5,556,645 | 9/1996 | Bockman et al. | 424/650 |
| 5,571,691 | 11/1996 | Conneely et al. | 435/69.1 |

OTHER PUBLICATIONS

Verma et al. (1997) Gene therapy–promises, problems and prospects. Nature 389:239–242, Sep. 1997.

*Primary Examiner*—Nancy Degen
*Assistant Examiner*—Robert Schwartzman
*Attorney, Agent, or Firm*—Whitham, Curtis & Whitham

[57] ABSTRACT

Estradiol facilitates non-viral gene delivery to breast tumor cells. The effect is dose dependent, and is independent of the gene construct, temperature, and tumor cell line. Thus, compositions and treatment regimens that use estradiol, or other estrogen pharmacologic agents, in combination with genes of interest can be used to provide targeted delivery and expression of genetic products in target cells and tissues of estrogen, such as breast cells. The compositions and treatment regimens have particular application to the enhanced delivery of genetic constructs useful in killing breast tumor cells and preventing tumor recurrence.

10 Claims, 3 Drawing Sheets

PHARMACO-GENE DELIVERY IN HUMAN BREAST CANCER CELLS

This invention was made using funds from grants from the National Institutes of Health, Grant Nos. 1F32CA6974501 and 1R01 CA55815, and the Department of Defense, Grant No. DAMD17-96-1-6167. The government may have certain rights in this invention.

DESCRIPTION

BACKGROUND OF THE INVENTION

1. Field of the Invention

The invention is directed to gene therapy and, more particularly, to the enhanced, non-viral delivery of genetic products to breast cancer cells.

2. Background Description

Current clinical therapeutic modalities for the treatment of breast cancer include chemotherapy and radiation treatment. These techniques effectively block the growth of breast cancer, and, in many cases, produce an apparent remission in this disease. However, there is often a recurrence of the disease, which may be a consequence of incomplete cell killing.

The reproductive hormone, estradiol, is typically found in the concentration range of 59–250 $\mu$M in menstruating females. Estradiol is used in the treatment of various benign clinical disorders such as vasometer symptoms associated with menopause, atrophic vaginitis, osteoporosis, hypoestrogenism, and has also been utilized in the therapy of selected breast cancer patients. Pharmacological concentrations of estradiol used for treating breast cancer patients are known to produce growth inhibition and cell killing in experimental models of breast cancer. However, incomplete cell killing by estradiol together with reactivation of dormant cytostatic cells can lead to tumor recurrence Viral gene delivery systems have been widely investigated. While these systems are relatively efficient, they are plagued by a number of problems including host toxicity, and immunogenic reactions. In addition, when viral carriers are used, there is the risk of delivering genomic mutations which can contribute to the reactivation of tumors and other maladies.

Recent clinical trials of non-viral, intra-tumor injection using lipid-based systems for gene-delivery have demonstrated that these methods are non-toxic and safe (see, Stewart et al., *Human Gene Therapy*, 3:267–275 (1992), and Hersh, *Cancer Gene Therapy*, Vol. 3, No. 6, 1996, p.S11). Lipofectamine™, a commercially available product available from Life Technologies of Gaithersburg, Md., is a lipid based liposome formulation which includes 3:1 w/w of the polycationic lipid 2,3-dioleyloxy-N-[2(sperminecarboxamido)ethyl]-N,N-dimethyl-1-propanaminium trifluoroacetate (DOSPA) and the neutral lipid dioleoyl phosphatidylethanolamine (DOPE) in membrane filtered water. This product has been used for the transfection of DNA into cultured eukaryotic cells. Product literature indicates one milliliter is sufficient for 50–200 transfections on 35 mm tissue culture dishes or 15–70 transfections on 60 mm dishes. However, these methods have also proven to be relatively inefficient in that low levels of the delivered genes are expressed in few target cells.

SUMMARY OF THE INVENTION

It is an object of this invention to provide a method for delivering genetic constructs via a non-viral mode with enhanced efficiency by co-administration with an estrogen pharmacologic agent.

It is another object of this invention to provide pharmaceutical genetic therapy preparations which include both an estrogen pharmacologic agent and a gene of interest.

It is yet another object of the invention to provide a method of treating breast tumor cells by providing genes which induce greater cell death in combination with an estrogen pharmacologic agent.

According to the invention, it has been determined that using an estrogen pharmacologic agent in combination with a gene of interest provides a distinct improvement in the efficiency of gene delivery to cells which have estrogen receptors as well as increasing the number of cells receiving the gene. In particular, estradiol, the most potent naturally occurring estrogen in mammals, at concentrations up to and including 100 $\mu$M, has been shown to facilitate the non-viral gene delivery of a variety of genetic constructs capable of performing their function (including apoptotic cell death) in human breast cancer cells. In addition, the pharmacological effects of estradiol in facilitating the gene delivery have been found to be concentration-dependent.

In a preferred embodiment of the invention, genes which can induce cell death are delivered via a non-viral route in combination with estrogen pharmacological compounds in order to provide more complete tumor remission and more effective prevention of tumor recurrence, thus leading to improved patient survival. The estrogen pharmacological agent (e.g., estradiol) can be administered via a different route from the gene, and need not be incorporated with the non-viral gene carrier (e.g., cationic lipid coat, etc.). In this embodiment, four classes of genes may be used. First, cytotoxic genes such a tumor necrosis factor alpha or the tumor suppressor gene p53 which promotes apoptosis can be provided. These genes would preferably be under the control of either a constitutive promoter or the egr-1 promoter which is selectively induced following ionizing radiation. For example, the gene of interest used in the practice of this invention could be an egr-1/TNF-alpha construct. Second, genes which sensitize cells by enzymatically activating pro-drugs can be provided. For example, thymidine kinase or cytosine deaminase, which respectively activate the cytotoxic pro-drugs gancylclovir and 5-fluorocytosine, could be provided. Third, genes which promote immune surveillance could be provided. For example, tumor growth factor-beta 1 could be provided in combination with interleukin-2 and interferon-gamma. Fourth, antimetastatic genes, such as 5 E1A, could be provided.

In the treatment of breast cancer, the pharmaceutical gene therapy combination, comprised of an estrogen pharmacologic agent (e.g., estradiol) and a gene of interest, will be injected into the breast tissue using a non-viral delivery system such as Lipofectamine™. Estradiol kills a fraction of human breast cancer cells. Simultaneously, estradiol increases the efficiency and fraction of residual cells receiving the delivered gene. Thus, following proposed pharmaco-gene therapy, the residual cells following estradiol treatment will be attacked by additional cytotoxic effects of the trans-gene with remarkably improved efficiency. Furthermore, the target selectivity can be enhanced if one uses the cytotoxic genes driven by an inducible promoter, rather than constitutive promoters. For instance, if a radiation inducible promoter such as egr-1 is used in the gene of interest construct, the patient will receive the additional benefit of tumor cell killing attributable to the radiation exposure.

This invention provides pharmacological gene targeting in the sense that the estradiol facilitates the gene delivery at the site of injection while limiting the gene delivery to non-target cells. Because the effect of estradiol on facilitating gene delivery is concentration-dependent, more genetic material will be delivered to the site of injection where the highest concentrations of estradiol will be provided. Significantly reduced concentrations of estradiol and negligible levels of the delivered gene are expected to reach undesirable sites, such as the uterus, upon direct injection of the pharmacological genetic therapy preparation into the breast because most of the estradiol/gene will be inactivated by serum and liver enzymes.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
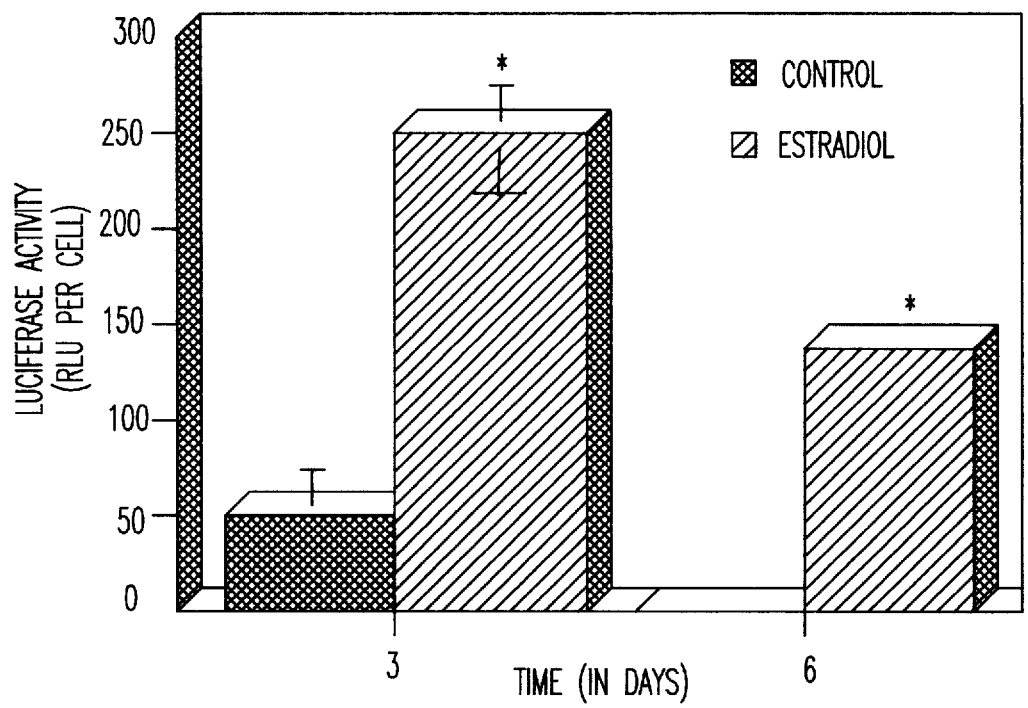
FIG. 1 is a bar graph showing the influence of estradiol on the expression of a pSV40-luciferase construct in MCF-7 breast tumor cells. MCF-7 cells were transfected with a PSV40 luciferase reporter construct in the absence or presence of 100 $\mu$M estradiol. Luciferase expression was assessed at days 3 and 6. Each value represents the mean ±SEM for replicate samples. * indicates values significantly different from corresponding controls. RLU is relative light units.

This invention is directed to the non-viral delivery of genetic material to target cells of estrogen pharmacologic agents. These include particularly breast, ovarian, uterine, brain, placental, and testicular cells, and possibly the adrenal cortex. A wide variety of estrogen pharmacological agents can be used. Estrogen broadly defines a major class of female sex hormones which include an 18-carbon steroid structure. The major estrogens are estrone and estradiol (17-$\beta$-estradiol), and the experiments presented herein with estradiol are representative of results that can be expected with other compounds within the class. Numerous ester and ether derivatives of estradiol are known or have been prepared at both hydroxy residues, including short chain alkyl ($C_{1-12}$) (e.g., estradiol 17$\beta$-cypionate), aryl (e.g, estradiol benzoate), and nitrogen containing moieties (e.g., estramustine), and it is known that the steroidal structure can be directly modified to include halogens, hydroxy (e.g., estriol), and other moieties. Any of these derivatives of estradiol, or derivatives of other estrogen compounds, could be used in the practice of this invention. Within the practice of this invention an estrogen pharmacologic agent includes any agent which has the basic estrogen structure, or which has been designed to three-dimensionally mimic this structure (e.g, tamoxifen), and which interacts with estrogen receptors on target cells.

Non-viral gene delivery can be accomplished by a number of well known techniques including physical methods including air gun, radiation, etc. and chemical methods including combining with cationic lipids, anionic lipids, polyamines, etc., and injecting the combination into the cell. In the preferred method of non-viral delivery of a gene of interest in the practice of this invention, cationic liposomal gene delivery systems are employed. While naked DNA can be delivered to eukaryotic systems, this approach is extremely inefficient because of barriers imposed by the size and charge of the DNA, as well as rapid enzymatic degradation of the DNA by the cell. Currently, the most widely used non-viral gene delivery system relies on the use of cationic lipids to form ionic bonds with the DNA, resulting the transport of the DNA-liposomal complex across cellular and nuclear membranes. Lipofectamine™ is a commercially available cationic lipid preparation available from Life Technologies, a division of GIBCO BRL, of Gaithersburg, Md., which is particularly advantageous in the practice of this invention. However, it should be understood by those of skill in the art that alternative lipid preparations, as well as different non-viral delivery systems may be employed in the practice of this invention.

Experiments discussed below demonstrate that the naturally occurring hormone, estradiol, produces a marked concentration-dependent enhancement in the delivery of genes to breast tumor cells. The increase in gene delivery was further improved by repeated exposure of the cells to the gene-liposome complex and estradiol combination. The control of gene delivery by estradiol has the potential of enhancing the amount of gene delivered to the breast tumor cell and increasing the gene product, both critical elements in the success of gene therapy. The non-viral gene delivery approach, which uses estradiol in combination with a gene of interest, can be used to improve the delivery of various genes to breast tumor cells. For example, specific genes of interest include suicide genes such as p53 and egr-1-TNF-alpha, cytotoxic pro-drug/enzymes such as gancyclovir/thymidine kinase and 5-fluorocytosine/cytosine deaminase, vaccines such as anti-tumor growth factor-beta 1, interleukin-2 and interferon-gamma, and antimetastatic genes such as 5 E1A. Experiments with p53 demonstrate the efficacy of the approach in facilitating the delivery and expression of p53 in tumor cells, thereby providing enhanced cell killing.

Materials and Methods

Materials—Dulbecco's Modified Eagle medium (DMEM, 56–439) was obtained from Hazelton Research Products of Denver, Pa.; L-glutamine, penicillin (10,000 u/ml), streptomycin (10 mg/ml), and fetal bovine serum were obtained from Whittaker Bioproducts of Walkersville, Md.; and defined bovine calf serum was obtained from Hyclone Laboratories, of Logan, Utah. Trypsin-EDTA, Lipofectamine™, and optiMEM were obtained from GIBCO BRL of Gaithersburg, Md. X-gal was obtained from Gold Biotechnology, Inc. of St. Louis, Mo. The pSV40-luciferase is available from Promega, and p-CMV-β-galactosidase is available from Clontech.

Cell-Culture—The MCF-7 breast tumor cell line was obtained from the National Cancer Institute, and the MDA-MB-231 cells were obtained from the Medical College of Virginia. Cells were maintained in Dulbecco's minimal essential media supplemented with 5% fetal calf serum (Life Technologies, Grand Island, N.Y.), 5% defined bovine serum, glutamine (29.2 mg/100 ml), amphotericin B (5 $\mu$g/ml) (Sigma Chemical), and penicillin/streptomycin (0.5 ml/100 ml). Approximately, $3-5\times10^4$ MCF-7 cells or $1\times10^4$ MDA-MB-231 cells were well were subcultured in six-well plates and allowed to grow for 2–3 days so as to achieve 60% confluency prior to conducting the gene delivery experiments. Preparation of DNA-liposome complex and optimization and transfection— Manufacturer's recommendations were followed for DNA-liposome complex preparation and optimization of the transfection condition to human breast cancer cells. Briefly, DNA was mixed with lipofectamine™ in serum free optimMEM media and incubated at room temperature for 45 minutes with gentle shaking every fifteen minutes. 6 $\mu$l of lipofectamine™ proved to be the optimal condition for transfection in these experiments. Because 2–4 $\mu$g of DNA per ml gave adequate results, 2 $\mu$g of DNA (1:1::SV-40 luciferase: CMV-βgalactosidase) and 6 $\mu$l of lipofectamine™ was used throughout the studies.

Trangene-liposomes and estradiol co-treatment—Estradiol was dissolved in a vehicle non-toxic to MCF-7 cells. Vehicle or estradiol (0 to 100 $\mu$M) was added to the media with DNA-liposome. The subconfluent culture of MCF-7 cells in six well plates were washed with optiMEM and then exposed to one ml of media containing DNA-liposome complex. Then, the cells were incubated at 37° C. in $CO_2$ incubator for five hours. 1 ml MEM media plus 20% of serum containing vehicle or estradiol was added and then further incubated overnight at 37° C. in $CO_2$ incubator for indicated times. In repeat transfection experiments, a similar process was performed twice on day 2.

Luciferase Reporter Assay—The cells transfected with pSV40-luciferase were washed twice with 2 ml PBS, and then lysed using 250 $\mu$l/well of reporter lysis buffer (Promega, Madison, Wis.) containing 125 mM Tris, pH 7.8 with $H_3PO_4$, 10 mM CDTA, 10 mM DTT, 50% glycerol and 5% triton X-100, and diluted 1:4 for 15 min. at room temperature. The cell lysate was scraped using a rubber policeman, collected in 1.5 ml microfuge tubes and centrifuged at 10,000 rpm for 2 min. at 4° C. The supernatant was transferred to a 1.5 ml Eppendorf tube and stored at –70° C. until used for the determination of luciferase activities.

The luciferase activity of the cellular extract was determined by mixing 20 $\mu$l of cell extract with 100 $\mu$m of Promega luciferase reagent containing 270 $\mu$M coenzyme A (lithium salt), 470 $\mu$M luciferin, 530 $\mu$M ATP, 20 mM tricine, 1.07 mM $(MgCO_3)_4Mg(OH)_2\cdot5H_2O$, 2.67 mM $MgSO_4$, 0.1 mM EDTA and 33.3 mM DTT pH 7.8 at room temperature. Relative Light Units (RLU) were measured for 20 seconds in a Berthold LB 9501 luminometer.

In a parallel experiment, the transfected cells were trypsinized to quantitatively evaluate viable cells utilizing hemocytometric trypan blue exclusion method. The luciferase was then expressed as RLU per viable cell. Histochemical staining for βgalactosidase expression— Cells were washed with PBS, and fixed with 2% paraformaldehyde at 4° C. for 5 minutes. Cells were allowed to stain dark blue following the formation of insoluble indigo derivative of X-gal, and end point of βgalactosidase activity.

Influence of Temperature—Influence of temperature was studied by treating cells with transgene in the presence or absence of estradiol for five hours at 37° C. in $CO_2$ incubator or at room temperature. After this, 2× transfection media was added and the treatment protocol discussed above was followed.

Statistical Analysis—All experiments were repeated at least once. Vehicle causes moderate increase in reporter activity was compared to untreated cells. Thus, influence of estradiol and vehicle on reporter activity was compared by ANOVA and $p<0.05$ was considered to be statistically significant. The statistical analysis was performed utilizing Statview 512™ McIntosh statistical software.

Results

Influence of estradiol on the delivery of pSV-40 luciferase and pCMV-βgalactosidase to MCF-7 cells In the first series of studies, the influence of continuous exposures to 100 $\mu$M estradiol on the expression of a luciferase reporter plasmid (under the control of an SV-40 promoter) in MCF-7 human breast tumor cells over a period of 2–6 days was determined. FIG. 1 shows that a five-fold increase in luciferase expression occurred upon treatment with 100 $\mu$M estradiol for three days, and a similar enhancement in expression was maintained through six days. Enhancement of gene delivery by estradiol was also demonstrated using a different reporter plasmid preparation, pCMV-βgalactosidase. Table 1 indicates that on days 3 and 6, expression of βgalactosidase was enhanced by 6.5-fold and 4.3 fold respectively as compared to corresponding controls.

TABLE 1

Influence of estradiol on the delivery of pCMV-βgalactosidase as evaluated by X-gal histochemical staining

| TREATMENT | DAY 3 | DAY 6 |
|---|---|---|
| Control | 3.55 ± 1.05[a] | 2.88 ± 0.55[a] |
| Estradiol | 23.31 ± 1.38[a] | 12.29 ± 2.11[a] |
| Fold increase | 6.5[b] | 4.3[b] |
| P Value (control vs Estradiol | 0.001 | 0.0037 |

[a]Each value represents the percent blue stained (X-gal positive) cells. The values are means ± SEM of triplicated samples.
[b]The increase in a fraction of cells receiving the pCMV-βgalactosidase vector upon treatment of estradiol was statistically significant at the level of the indicated P value.

The results reported in Table 1, along with other studies performed using the histochemical indicator X-gal and microscopic examination of individual cells, demonstrated that the overall percentage of MCF-7 cells expressing pCMV-βgalactosidase was increased together with expression of pβgalactosidase in individual cells. Thus, the increase in gene expression is related to the accumulation of the gene in more cells as well as the greater accumulation of the gene in individual cells.

Figure 2:
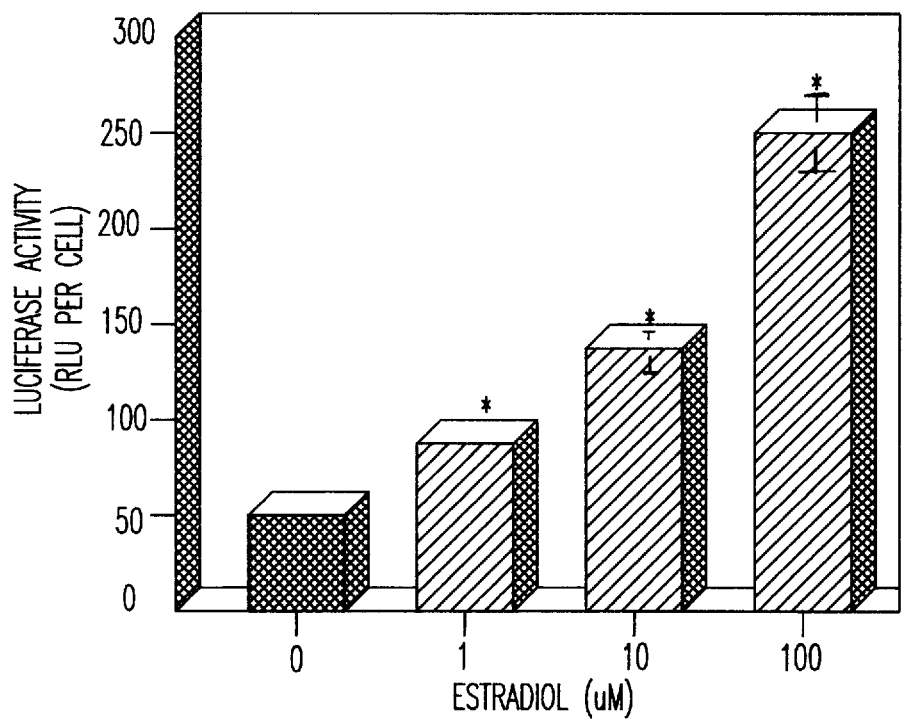
FIG. 2 is a bar graph showing the concentration-dependent facilitation of gene delivery to MCF-7 human breast cancer cells. The MCF-7 cells were transfected with pSV40-luciferase vector in the absence or presence of 1–100 $\mu$M estradiol. The luciferase activity was evaluated after three days and expressed as RLU per cell. Each value represents the mean±SEM for replicate samples and * indicates values significantly different from corresponding controls.

FIG. 2 shows that the enhancement of gene delivery by estradiol was concentration dependent. FIG. 2 shows approximately 1.5, 2.5, and 5.3-fold induction of luciferase expression from the pSV40 luciferase construct following treatment with 1 μM, 10 μM and 100 μM estradiol.

Influence of estradiol on delivery of pSV-40 luciferase to MDA-MB23 1 cells:

MCF-7 cells are estrogen receptor positive. Because of this, it appeared possible that the effects of estradiol on gene delivery might be related to its association with the estrogen receptor. In order to address this possibility, studies were designed to assess the influence of estradiol on gene delivery to MDA-MB231 cells, which are estrogen receptor negative. As shown in Table 2, the increase in gene delivery to MDA-MB231 cells by 100 μM estradiol was at least comparable to the effect observed in MCF-7 cells. However, MDA-MB 231 cells were less responsive than MCF-7 cells at lower concentrations of estradiol.

TABLE 2

Delivery of pSV40-luciferase to MDA-MB-231 human breast cancer cells upon treatment with estradiol for three days

| Estradiol (μM) | Luciferase activity (RLU/cell) |
| --- | --- |
| 0 | 2.27 ± 0.16[a] |
| 0.1 | 2.84 ± 1.02[a] |
| 100 | 128.44 ± 13.47[a,b] |

[a]Each value is the mean ± SEM of quadruplicate samples.
[b]The values were significantly (p < 0.05) higher than control.

Figure 3:
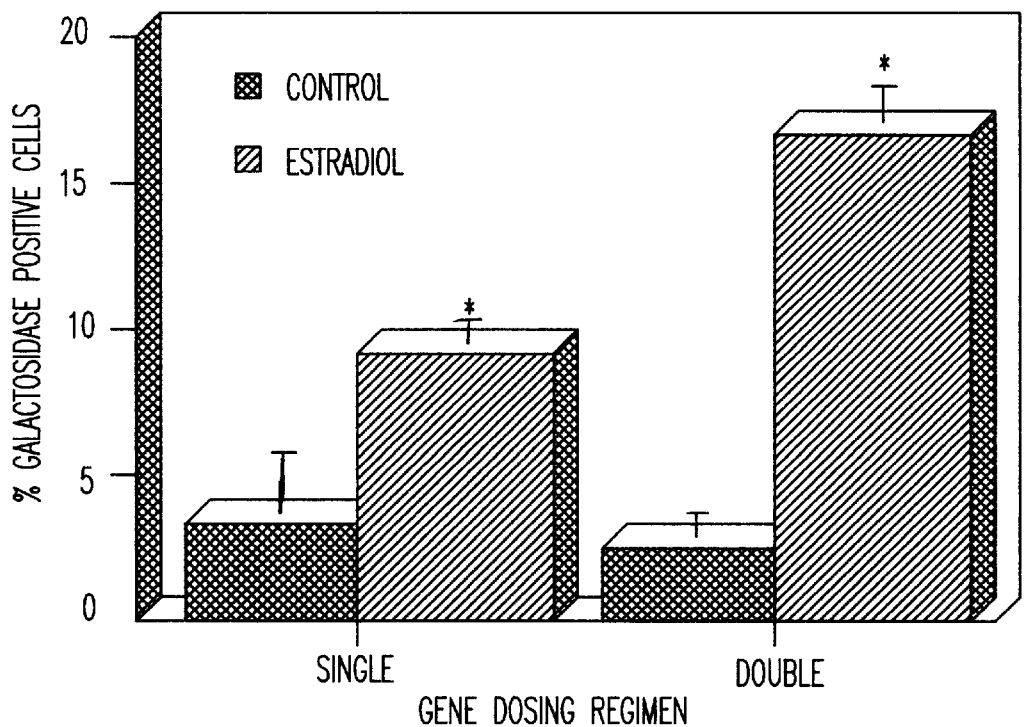
FIG. 3 is a bar graph showing gene delivery to MCF-7 human breast cancer cells after a single or double dose-regimen. Stained cells and non-stained cells indicating the presence or absence of transfected gene respectively were counted on day 6. There was a greater delivery of gene upon double transfection as compared to single transfection. Each value represents mean±SEM for triplicate samples. * indicates values significantly different from corresponding controls.

Enhancement of gene delivery by repeated treatment with estradiol:

Repeated dosing regimens are commonly used strategies in achieving a desired therapeutic level of clinical agents. Experiments were conducted to determine if a repeated exposure of MCF-7 cells to estradiol combined with liposomal gene delivery system could improve gene delivery. FIG. 3 indicates that a repeat exposure to estradiol, lipofectamine™, and the plasmid of interest, in this case, pCMV-βgalactosidase, resulted in an approximately 1.8 to 2.6 fold further improvement in potentiation of gene delivery over that observed after a single dosing regimen.

Figure 4:
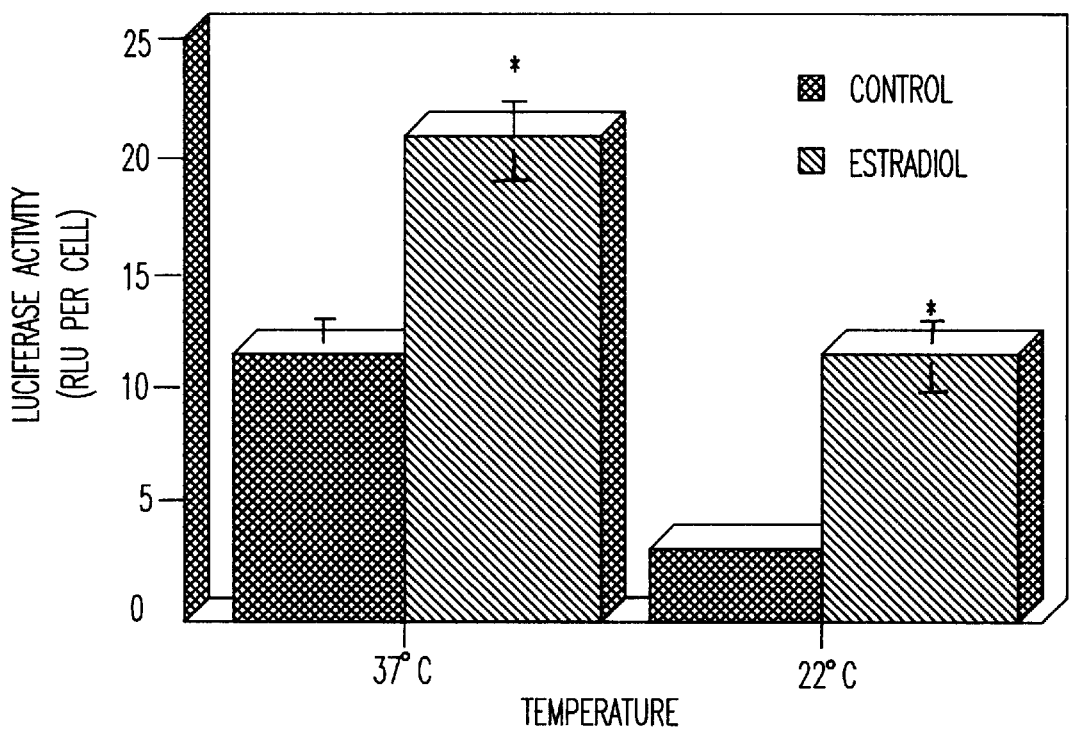
FIG. 4 is a bar graph showing the influence of temperature on the facilitation of pSV40 luciferase gene delivery to MCF-7 human breast cancer cells by estradiol. MCF-7 cells were transfected with a pSV40 luciferase reporter construct in the absence or presence of 100$\mu$M estradiol for five hours at room temperature and 37° C., washed and then reincubated at 37° C. to assess luciferase expression on day 3 as described above. Each value represents mean ±SEM for four replicate samples. * indicates values significantly different from corresponding controls.
Figure 5:
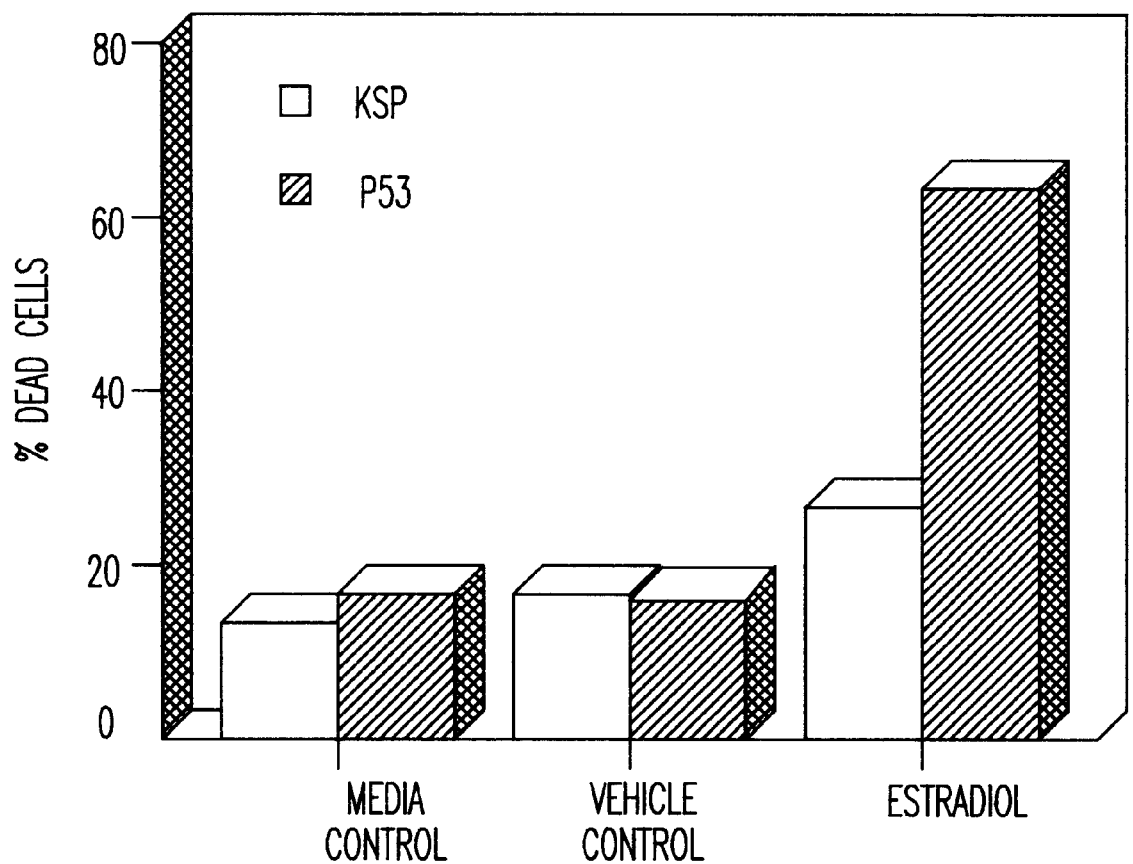
FIG. 5 is a bar graph showing estradiol (100 $\mu$M) together with void gene (i.e., blue script gene, ksp) causes greater killing of MDA-MB-231 cells which were treated with the void or even p53 apoptotic gene together with media or vehicle. The killing of MDA-MB-231 cells caused by pharmacological treatment with estradiol (100 $\mu$M) and p53 apoptotic gene is remarkably greater than that following treatment of estradiol with void vector (indicated by arrow).

Influence of temperature on estradiol enhanced gene delivery:

Experiments were conducted to determine if the improvement in the efficiency of gene delivery was related to energy dependent processes such as endosomal transport and its intracellular trafficking. To investigate this possibility, the influence of reducing the incubation temperature on estradiol mediated enhancement of gene delivery was studied. FIG. 4 shows that at 22° C. (room temperature), the expression of pSV40-luciferase was reduced in both control and estradiol-treated cells. However, the extend of enhancement of gene delivery was comparable at 37° C. and at 22° C.

The experiments discussed above demonstrated that following chronic treatment of MCF-7 breast tumor cells with estradiol, a striking improvement in the constitutive expression of two different plasmids, pSV-40 luciferase and pCMV-βgalactosidase, was observed. This is considered to be an end point for determining the successful delivery of an expressible gene. The observed increase in the efficiency of delivery of two distinct DNA sequence plasmids to MCF-7 cells upon treatment with estradiol indicates that the enhancement of gene delivery is independent of the DNA sequence of the plasmid. In addition, while heterogenous delivery of the pCMV-galactosidase gene was observed in only a small fraction of MCF-7 cells under control conditions, estradiol treatment increased the number of cells receiving the exogenous DNA as well as the amount of DNA delivered to each cell.

The experiments also demonstrated that estradiol enhances gene delivery subsequent to a repeated administration of the liposomal-DNA complex. This indicates that the improvement of gene delivery by estradiol is not limited to a single treatment. These effects are similar to other biological actions of estradiol which involve repeated administration such as in the treatment of osteoporesis and breast cancer. Repeated administration improving the effectivity of gene therapy is particularly useful for using gene as a sustained release medicine. In other words, the repeat transient transfection can achieve the same desired purpose of long-term gene expression as is achieved by permanent transfection, but with the added advantage of shutting down expression (by not repeating the dose) if desired.

Enhancement of gene delivery by estradiol was also observed in the estrogen receptor negative MDA-MB-231 human breast tumor cell line. This observation indicates that the estrogen receptor is unlikely to play a predominant role in the improvement of gene delivery by estradiol.

The delivery of gene in control cells was energy dependent as luciferase reporter activity in control cells which were incubated at 37° C. was double that in cells incubated at 22° C. Such data is consistent with the suggested energy dependent mechanism of lipid gene delivery systems such as endocytic mechanisms. Conversely, the effects of estradiol on gene delivery to MCF-7 cells was energy independent since enhancement was observed at both 37° C. and 22° C.

These results indicate that targeted, non-viral delivery of genetic constructs can be achieved and enhanced when a gene of interest is used in combination with estradiol. The invention has particular application in the treatment of breast cancer. This would be accomplished by in the following ways:

Combined ex vivo treatment: The therapeutic gene (vaccine gene such as TGF-B, interleukins and other immunomodulators, etc.) and pharmacological agent (estrogen-estradiol) as a combined formulation can be used for transfecting the cells (derived from biopsy tissue) of the patient and then re-injected at target site. As a result of such injection, powerful antibodies will accumulate in target and then destroy the target Combined in vivo local treatment: The therapeutic gene and pharmacological agent (estrogen-estradiol) as combined formulation can be directly injected at target site (breast tissue).

Separate in vivo pharmacological treatment: If the therapeutic effects of the gene is desired at multiple targets, then the gene can be administered systemically, and the estrogen pharmacologic agent is administered locally into the target tissue. If systemic toxicity of estradiol is not a problem, then estraderm patches can be used, provided they deliver a high concentration of estradiol, for getting the desired systemic concentration of estrogen, and the gene can be administered either locally or systemically.

Miscellaneous routes of pharmaceutical administration for combined pharmaco-gene therapy: intra-arterial administration-if accumulation is desired to a particular organ; intrathecal administration if multiple drug resistance (MDR) gene needs to protect bone against toxicity of ionizing radiation, chemotherapy and cytotoxic gene therapy; other local administration where steroids are regularly uses (e.g., rectal, vaginal, nasal) for combating inflammatory responses. In these situations the genes synthesizing superoxide dismutase will be utilized to quench free radicals, which is the key factor for evoking inflammatory responses.

In all of the above administration routes the overall formulation can be designed in sustained release form by either manipulating both gene and estrogen by trapping them in various kinds of liposomes or simply using slow-release forms of estrogen. The pharmacological gene therapy of this invention has many advantages in managing the dosing regimen. For instance, there can be a pseudo-long sustained release characteristic following multiple repeat administration, a pseudo-short sustained release following single dose administration, and the level of the gene reaching the target can be manipulated by both altering the quantity of gene delivered and by the concentration of pharmacological agents administered.

EXAMPLE

Experiments were conducted which demonstrate that MDA-MB-231 cells treated with estradiol together with p53 resulted in greater cell death than cells treated with estradiol alone. Thus, estradiol, which is known to have cytotoxic effects on MDA-MB-231 cells, also enhances the uptake and expression of p53 in MDA-MB-231 cells which leads to apoptosis and further cell death.

While the invention has been described in terms of its preferred embodiments, the invention can be practiced with modification and variation within the spirit and scope of the appended claims.

We claim:

1. A composition for gene delivery, comprising:
   a gene of interest; and
   estradiol.

2. The composition for gene delivery of claim 1 further comprising a lipid carrier, said gene of interest being associated with said lipid carrier.

3. The composition for gene delivery of claim 1 wherein said gene of interest is selected from the group consisting of cytotoxic genes and antimetastatic genes.

4. The composition for gene delivery of claim 1 wherein said gene of interest is selected from the group consisting of p53, tumor necrosis factor, thymidine kinase, cytosine deaminase, 5 E1A, and TGF-beta.

5. The composition for gene delivery of claim 1 wherein said gene of interest includes a constituitive promoter.

6. The composition for gene delivery of claim 1 wherein said gene of interest includes an inducible promoter.

7. The composition for gene delivery of claim 1 wherein said gene of interest and said estradiol are present in a liquid composition.

8. The composition for gene delivery of claim 2 wherein said lipid carrier is comprised of a mixture of cationic lipids.

9. The composition for gene delivery of claim 4 wherein said gene of interest is p53.

10. The composition for gene delivery of claim 6 wherein said inducible promoter is egr 1.

* * * * *